(12) United States Patent
Houwen et al.

(10) Patent No.: US 6,900,023 B1
(45) Date of Patent: May 31, 2005

(54) METHOD FOR CLASSIFYING AND COUNTING LEUKOCYTES

(75) Inventors: Berend Houwen, Redlands, CA (US);
Fu-sheng Wang, Claremont, CA (US);
Hiroyuki Fujimoto, Hyogo (JP);
Takashi Sakata, Hyogo (JP); Yukio Hamaguchi, Hyogo (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/388,899

(22) Filed: Sep. 2, 1999

(51) Int. Cl.⁷ .............................................. G01N 33/53

(52) U.S. Cl. ........................... 435/7.24; 435/2; 435/7.2; 435/239; 435/287.1; 435/288.7; 435/962; 436/10; 436/17; 436/56; 436/63; 436/164; 436/165; 436/174; 436/175; 436/546; 436/800; 436/824; 436/825

(58) Field of Search ............................. 435/2, 7.2, 7.1, 435/7.21, 7.23, 7.24, 7.32, 7.92, 239, 243, 962, 963, 287.1, 288.7; 436/8, 10, 171, 174, 175, 176, 526, 532, 533, 546, 800, 824, 875, 65, 63, 164, 165, 825; 356/33, 39, 336, 338

(56) References Cited

U.S. PATENT DOCUMENTS

| | | | |
|---|---|---|---|
| 5,137,809 A | | 8/1992 | Loken et al. |
| 5,413,938 A | | 5/1995 | Tsujino et al. |
| 5,646,001 A | * | 7/1997 | Terstappen et al. ......... 435/7.21 |
| 5,776,709 A | * | 7/1998 | Jackson et al. .............. 435/7.2 |
| 5,840,502 A | * | 11/1998 | Van Vlasselaer ........... 435/7.21 |

FOREIGN PATENT DOCUMENTS

| | | | | |
|---|---|---|---|---|
| GB | 0 317 156 | * | 5/1889 | .................. 435/7.2 |

OTHER PUBLICATIONS

Hubl et al., Toward a new reference method for the leucocyte five–part differential, Cytometry 30: 72–84 (1997).*
McCarthy et al., A simple flow cytometric procedure for the determination of surface antigens on unfixed leucocytes in whole blood, Journal of immunological Methods, 163: 155–160 (1993).*
Macey et al., Hoe should CD34 + cells br analyzed? A study of three classes of antibody and five leucocyte preparation procedur s, Journal of Immunological Methods, 204: 175–188 (1997).*

(Continued)

Primary Examiner—Long V. Le
Assistant Examiner—Gailene R. Gabel
(74) Attorney, Agent, or Firm—Bryan Cave LLP

(57) ABSTRACT

A method for classifying and counting leukocytes comprises the steps of: (1) adding to a hematological sample the following fluorescence-labeled antibodies labeled with fluorescent dyes which emit fluorescences distinguishable from each other; (a) a first fluorescence-labeled antibody (1st antibody) which bonds specifically to leukocytes, (b) a second fluorescence-labeled antibody (2nd antibody) which bonds to at least one kind of neutrophilic cells, and (c) a third fluorescence-labeled antibody (3rd antibody) which bonds to at least one kind of immature granulocytic cells, in order to stain leukocytic cells in the sample, and removing erythrocytes from the sample; (2) analyzing the resulting sample using a flow cytometer to measure at least one scattered light signal and three separate fluorescence signals; (3) defining a group of granulocytic cells on the basis of intensity of the scattered light and intensity of fluorescence from the 1st antibody; (4) defining neutrophilic cells in the defined group of granulocylic cells on the basis of the intensity of the fluorescence from the 1st antibody and intensity of fluorescence from the 2nd or 3rd antibody; (5) classifying the defined group of the neutrophilic cells into groups of neutrophilic cells different in degree of maturity on the basis of the intensity of the fluorescence from the 2nd antibody and the intensity of the fluorescence from the 3rd antibody, and counting the number of cells in each of the groups.

15 Claims, 7 Drawing Sheets

OTHER PUBLICATIONS

Festin et al., Multicolor flow cytometric analysis of the CD45 antigen provides improved lymphoid cell discrimination in bone marrow and tissue biopsies, Journal of Immunological Methods, 177:215–224 (1994).*

Hashimi et al., Cytofluorometric detection of chronic myelocytic leukemia supervening in a patient with chronic lymphocytic leukemia, American Journal of Medicine, 80 (2): 269–275 (1986).*

Gopinath et al., Identification og Eosinophils in Lysed Whole Blood ysuing Side Scatter and CD16 Negativity, Cytometry 30: 313–316 (1997).*

Boven, K.L., Davis, B.H.; Laboratory Hematology, vol. 3, No. 4, 1997 "Abnormal Patterns of Expression of CD16 (FcRgIII) and CD11b (CRIII) Antigens by Developing Neutrophils in the Bone Marrow of Patients with Myelodysplastic Syndrome," pp. 292 to 298.

Hubl, M.D., Wolfgang; Andert, M.D., Sylvia; Thum, Gabriele; Ortner, Sabine; and Bayer, M.D., Peter Michael; Feb. 1997; Am. J. Clin. Patholo., vol. 107, No. 2; "Value of Neutrophil CD16 Expression for Detection of Left Shift and Acute–Phase Response," pp. 187–196.

* cited by examiner

Intensity of the red fluorescence

Int nsity of the gre n fluorescence

METHOD FOR CLASSIFYING AND COUNTING LEUKOCYTES

BACKGROUND OF THE INVENTION

1. Field of the Invention

The present invention relates to a method for classifying and counting leukocytes, more particularly a method for classifying and counting leukocytes which allows immature granulocytes different in degree of maturity to be classified and counted by a flow cytometry.

2. Description of Related Art

In the field of clinical examination, classifying and countering immature granulocytes according to the degree of maturity is advantageous since it provides significantly useful information for making a correct diagnosis of a disease and for observing the course of a disease.

For example, immature granulocytes normally exist in bone marrow but do not exist in peripheral blood. For this reason, the presence of immature granulocytes in peripheral blood of a patient indicates the possibility that the patient has an infectious disease, inflammatory disease, chronic or acute myelocyticleukemia, malignant tumor or other disease. Accordingly, classifying and enumerating immature granulocytes different in the degree of maturity is helpful for diagnosing these diseases and for monitering the progress of the diseases.

Conventionally, a common method for classifying and counting immature granulocytes is comprised of preparing a smear sample of blood, staining the sample with a suitable dye, microscopically classifying cells in the sample into categories of promyelocytes, myelocytes and metamyelocytes according to their degree of maturity, and counting cells in each category. However, this method requires a complicated pretreatment before microscopic observation. Accuracy of the method is poor because only a limited number of cells can be counted. Furthermore, considerable skill of the operator is required for accurate classification. Reproducibility is limited due to the small number of leukocytes enumerated.

On the other hand, a variety of methods utilizing the principle of flow cytometry have been proposed for analysis of blood components in marrow fluid which contains blood cells in various stages of maturity.

For example, U.S. Pat. No. 5,137,809 has proposed a method for identifying different cell series and stages of maturity of cells in marrow fluid using a first antibody for indicating leukocytes and a second antibody for classifying leukocytes into subpopulations. However, this method has a problem in that immature granulocytes cannot be classified according to their degree of maturity as by microscopic observation, because the stages of maturity are indicated only by one parameter, i.e., the second antibody.

Bowen et al have reported that the intensity of expression of CD 16 and CD11b reflects the degree of maturity of granulocytic cells in bone marrow (Abnormal patterns of expression of CD16(FcRgIII) and CD11b(CRIII) antigens by developing neutrophils in the bone marrow of patients with myelodysplastic syndrome (Laboratory Hematology, Vol.3, No.4, 292 to 298,1997)). According to this report, granulocytic cells are first indicated with CD45 and SSC (side scattered light) and the degree of maturity of the granulocytic cells can be judged by checking the intensity of expression of CD16 and CD11b in the granulocytic cells. However, this method cannot distinguish mature eosinophils from immature granulocytes and therefore analysis results are poor. Particularly, both mature eosinophils and immature granulocytes are CD16-negative and CD11b-negative and cannot be separated from each other.

For analyzing leukocyte components in a sample of peripheral blood, a variety of methods have been proposed.

For example, U.S. Pat. No. 5,413,938 has proposed a method for measuring immature granulocytes by lysing mature leukocytes with a reagent containing a nonionic surfactant and an amino acid. However, according to this method, all leukocytes except immature granulocytes are lysed and thus cannot be enumerated. Therefore, this method alone cannot calculate the ratio of an immature granulocyte count to a leukocyte count.

Hūbl et al have reported a method for detecting immature neutrophils on the basis of expression of CD16 (Value of neutrophil CD16 expression for detection of left shift and acute-phase response; Am. J. Clin. Pathol., 107(2): 187–196, February 1997). However, this method does not describe a method for classifying immature granulocytes according to the degree of maturity.

Under these circumstances, there is a demand for a method for accurately counting immature granulocytes in peripheral blood independently of effect of other leukocytic cells and classifying the immature granulocytes according to their degree of maturity.

SUMMARY OF THE INVENTION

The present invention provides a method for classifying and counting leukocytes comprising the steps of:

(1) adding to a hematological sample the following fluorescence-labeled antibodies labeled with fluorescent dyes which emit fluorescences distinguishable from each other;
   (a) a first fluorescence-labeled antibody which bonds specifically to leukocytes,
   (b) a second fluorescence-labeled antibody which bonds to at least one kind of neutrophilic cells, and
   (c) a third fluorescence-labeled antibody which bonds to at least one kind of immature granulocytic cells,
in order to stain leukocytic cells in the hematological sample, and
removing erythrocytes from the hematological sample;

(2) analyzing the resulting hematological sample using a flow cytometer to measure at least one scattered light signal and three separate fluorescence signals;

(3) defining a group of granulocytic cells on the basis of intensity of the scattered light and intensity of fluorescence from the first fluorescence-labeled antibody;

(4) defining neutrophilic cells in the defined group of granulocylic cells on the basis of the intensity of the fluorescence from the first fluorescence-labeled antibody and intensity of fluorescence from the second or third fluorescence-labeled antibody;

(5) classifying the defined group of the neutrophilic cells into groups of neutrophilic cells different in degree of maturity on the basis of the intensity of the fluorescence from the second fluorescence-labeled antibody and the intensity of the fluorescence from the third fluorescence-labeled antibody, and
counting the number of cells in each of the groups different in the degree of maturity.

These and other objects of the present application will become more readily apparent from the detailed description given below. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
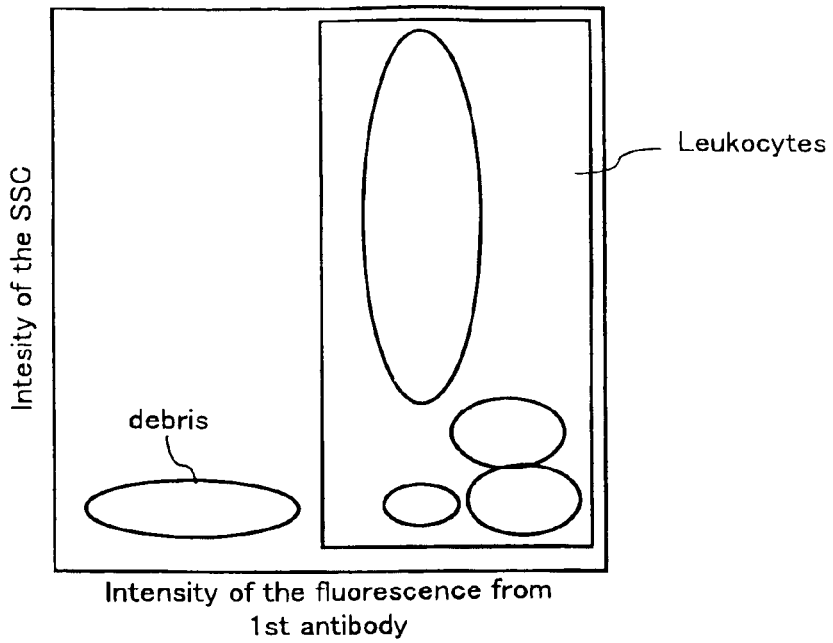
FIG. 1 is a scattergram for identifying the whole leukocyte group.

In the present invention, the hematological sample used in step (1) means a sample of body fluid such as peripheral blood, bone marrow fluid, urine or a sample collected by apheresis, of a mammal, especially a human. Such hematological samples may be subjected to the steps of the present invention either directly after being collected or after heparin or other anticoagulant is added thereto in an appropriate amount, for example.

The type of the antibody of the first fluorescence-labeled antibody which bonds specifically to leukocytic cells is not particularly limited provided that it bonds specifically to various kinds of leukocytes, such as monocytes, lymphocytes, neutrophils, eosinophils and basophils. For example, an anti-CD45 antibody may be mentioned. As this antibody, a commercially available one may be used.

The antibody of the second fluorescence-labeled antibody which bonds to neutrophilic cells is an antibody capable of recognizing an antigen which exists on the surface of neutrophilic cells in varying densities depending upon the degree of maturity of the neutrophilic cells and boding to the neutrophilic cells. The type of the antibody is not particularly limited, provided that it bonds to one kind of or two or more kinds of promyelocytes, myelocytes, metamyelocytes, band forms, segmented forms and the like. For example, an anti-CD11b, an anti-CD16, an anti-CD66b and an anti-CD66c antibodies may be mentioned. The antibody of the second fluorescence-labeled antibody may bond to other cells such as monocytes, eosinophils, lymphocytes and the like provided that it bonds to the above-described antigen. As the antibody, a commercially available one may be used.

The antibody of the third fluorescence-labeled antibody which bonds to immature granulocytic cells is an antibody capable of recognizing an antigen which exists on the surface of immature granulocytic cells in varying densities depending upon the degree of maturity of the immature granulocytic cells and bonding to the immature granulocytic cells. The type of the antibody is not particularly limited, provided that it bonds to one kind of or two or more kinds of promyelocytes, myelocytes, metamyelocytes and the like. For example, the anti-CD11b, anti-CD16, anti-CD66b and anti-CD66c antibodies may be mentioned. However, it is noted that the antibody of the third fluorescence-labeled antibody is required to differ from that of the second fluorescence-labeled antibody used. The antibody of the third fluorescence-labeled antibody may bond to other cells such as monocytes, eosinophils, lymphocytes and the like provided that it bonds to the above-described antigen.

In the present invention, the antibodies of the second and third fluorescence-labeled antibodies may be any combination of the anti-CD16 antibody with the anti-CD11b antibody, the anti-CD16 antibody with the anti-CD66b antibody, the anti-CD16 antibody with the anti-CD66c antibody, the anti-CD11b antibody with the anti-CD66b antibody and the anti-CD11b antibody with the anti-CD66c antibody, for example. Among these combinations, the combination of the anti-CD 16 antibody and the anti-CD11b antibody is preferable.

As fluorescence-labeling compounds for the above-mentioned antibodies, labeling compounds such as fluorescein isothiocyanate (FITC), phycoerythrin (PE), allophicocyanin(APC), Texas Red, PE-CY5 and peridinin chlorophyll protein (PerCP) may be mentioned. The fluorescence-labeling compounds to be bonded to the three antibodies used in the present invention are required to have spectra different from each other. For example, a combination of FITC, PE and PE-CY5 and a combination of FITC, PE and PerCP may be metnioned.

The mixture ratio of the fluorescence-labeled antibodies to the hematological sample may be adjusted as appropriate depending upon the state of the hematological sample, the types of the fluorescence-labeled antibodies and the like. For example, the mixture ratio (the antibodies: the hematological sample) by volume may be 1:20 to 1:2. Incubation temperature and incubation time at this step may be adjusted depending upon the mixture ratio of the fluorescence-labeled antibodies to the hematrogical sample and the like. For example, they may be allowed to incubate for 15 to 30 minutes at room temperature or higher and for 30 to 40 minutes at lower temperature for instance 0 to 10° C. When the fluorescence-labeled antibodies are added to the hematological sample, the first, second and third fluorescence-labeled antibodies may be added to the hematological sample in this order or in any other order. Alternatively, the first, second and third fluorescence-labeled antibodies may be mixed separately from the hematological sample and then the resulting mixture may be added to the hematological sample.

Erythrocytes are removed from the hematological sample. The removal of erythrocytes is carried out for purpose of avoiding effect of erythrocytes which may disturb measurement of leukocytes by flow cytometry in a later step. Erythrocytes may be removed from the hematological sample by treating the sample with dextran to precipitate erythrocytes, by treating the sample with a specific gravity liquid such as Ficoll-Hypaque to separate leukocytes from erythrocytes or by treating the sample with a reagent which gives damage to erythrocytes so as to lyse erythrocytes. Among such treatments, the treatment of the sample with an ammonium chloride based hemolysing agent for lysing erythrocytes is preferable because this treatment is simple to operate and damages few leukocytes.

In step (1) of the present invention, erythrocytes may be removed from the hematological sample before leukocytes in the sample are stained with a fluorescence-labeled antibody, after the leukocytes are stained with the fluorescence-labeled antibody, or between sub-steps of adding the first to third fluorescence-labeled antibodies to the sample, provided that the accomplishment of the later steps (3) to (6) which are described below is not affected adversely.

The flow cytometer used in step (2) is not particularly limited and any type of flow cytometer may be used. At least one signal representative of scattered light and three signals representative of fluorescence should be detected with regard to the above obtained hematological sample by the flow cytometer.

Scattered light generally measurable by flow cytometers includes forward scattered light (FSC) and side scattered light (SSC). In the present invention, the side scattered light is preferred since the side scattered light signal increases its intensity depending upon the size of a cell and the amount of granules and/or structures contained in the cell. The fluorescence to be detected varies depending upon the types of labeling characteristics of the fluorescence-labeled antibodies used. For example, a combination of green fluorescence, orange fluorescence and red fluorescence may be mentioned.

In steps (3) to (5), immature granulocytes different in the degree of maturity are classified and counted from at least one scattered light signal and three fluorescence signals.

Figure 2:
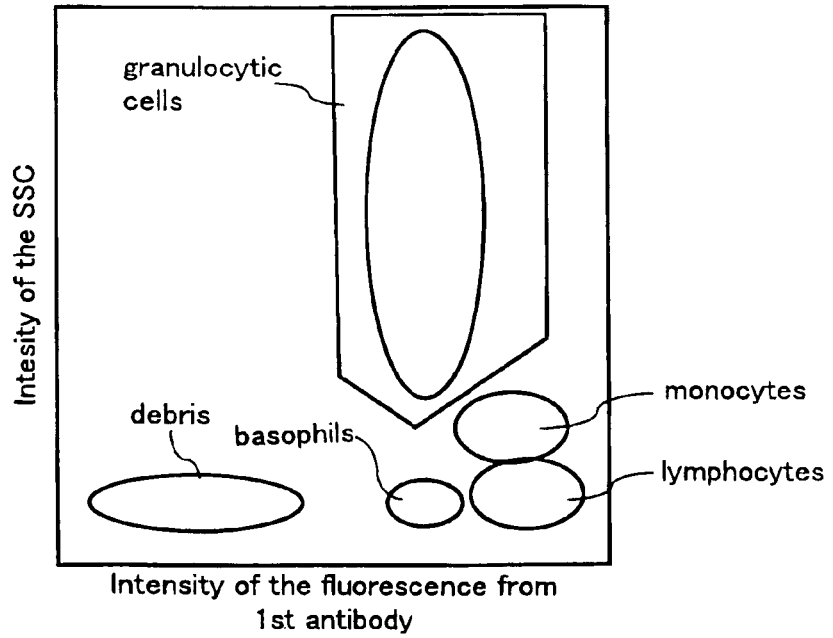
FIG. 2 is a scattergram for identifying granulocytes only (neutrophils and eosinophils)

First, in step (3), the group of granulocytic cells (including immature granulocytes and mature neutrophils and eosinophils) are identified on the basis of the intensity of the scattered light and the intensity of the fluorescence from the first fluorescence-labeled antibody. More particularly, the intensity of the scattered light and the intensity of the fluorescence from the first fluorescence-labeled antibody are measured and a two-dimensional distribution map (e.g., a scattergram) is produced with both the intensities plotted in two axes. Thereby, the group of granulocytic cells including immature granulocytes can be separated from monocytes, lymphocytes, basophils and debris which are erythrocytes remaining in the sample and/or pieces of erythrocytes destroyed by the hemolytic treatment (see FIG. 2).

In the two-dimensional distribution map, monocytes, lymphocytes, basophils and debris can be each identified as well as granulocytic cells including immature granulocytes as described above. Thereby the full leukocyte counts can be calculated by defining a group including the groups of all granulocytic cells including immature cells, monocytes, lymphocytes and basophils (see FIG. 1).

Figure 3:
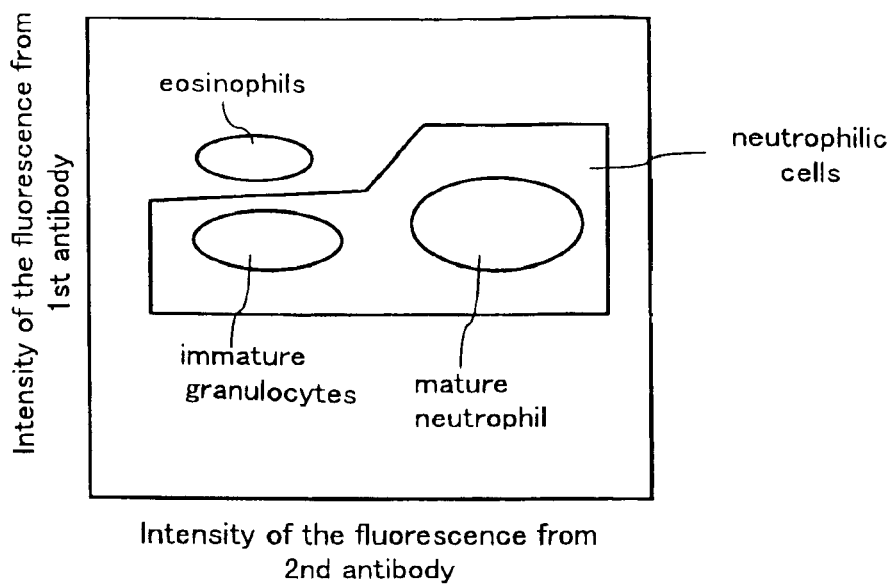
FIG. 3 is a scattergram for identifying neutrophilic cells only.

Subsequently, in step (4), the intensity of the fluorescence from the first fluorescence-labeled antibody and the fluorescence from the second or third fluorescence-labeled antibody are measured in the identified group of granulocytic cells, thereby to identify the group of neutrophilic cells (mature neutrophils and immature granulocytes). For this measurement, the characteristic of eosinophils regarding antigen density can be utilized. For example, if the anti-CD45 antibody and the anti-CD16 antibody are used as the first antibody and second antibody, mature neutrophils are positive to the anti-CD16 antibody while eosinophils and immature granulocytes are negative to the anti-CD16 antibody. However eosibophils have a higher density of antigens to the anti-CD45 antibody than immature granulocytes. Therefore, by producing a two-dimensional distribution map with the intensity of the fluorescence from the first fluorescence-labeled antibody and the intensity of the fluorescence from the second fluorescence-labeled antibody plotted, neutrophils can easily be separated from eosinophils (see FIG. 3).

Figure 4:
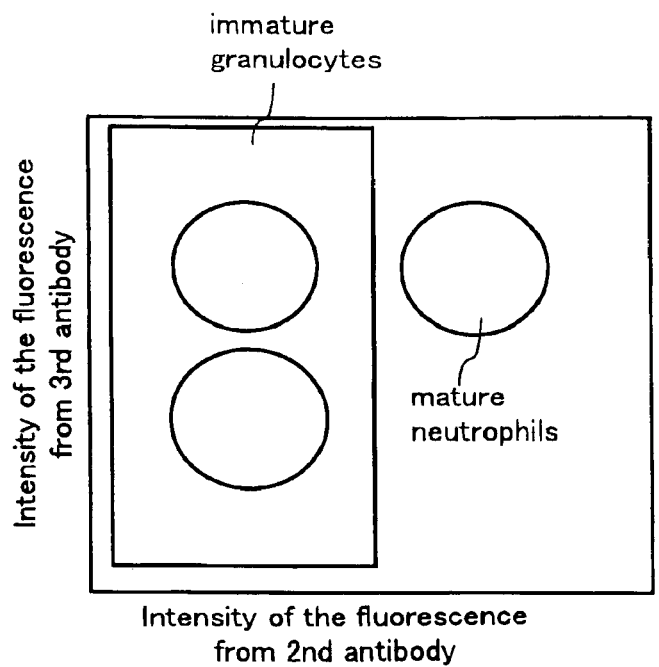
FIG. 4 is a scattergram for identifying immature granulocytes.
Figure 5:
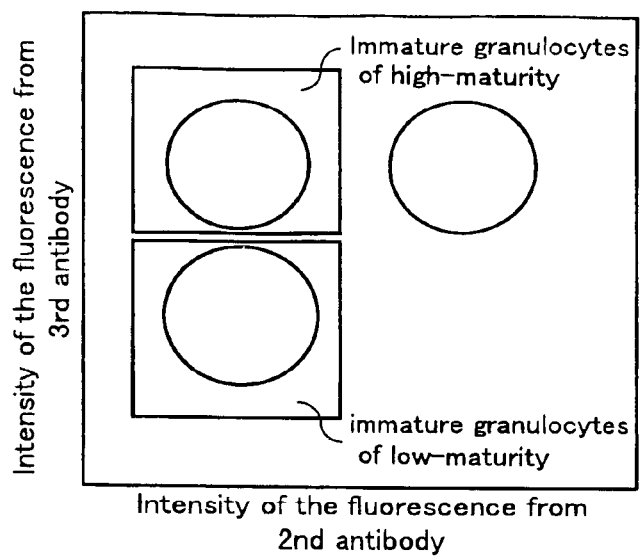
FIG. 5 is a scattergram for identifying groups of immature granulocytes different in degree of maturity.

Further, in step (5), the intensities of the fluorescences from the second and third fluorescence-labeled antibodies are measured in the identified group of neutrophilic cells (mature neutrophils and immature granulocytes), thereby to identify immature granulocytes and further classify the immature granulocytes according to their degree of maturity. As the second and third antibodies used for this purpose, antibodies whose corresponding antigens change their expression according to the course of maturity of neutrophilic cells may be selected. However, for more effective classification according to the degree of maturity, the antigens should preferably be different according to time of expression. For this reason, the second and third antibodies should preferably be a combination of the anti-CD16 antibody and the anti-CD11b antibody. More particularly, in the course of maturation of neutrophilic cells, antigens CD16 and CD11b appear on the surface of the neutrophilic cells as the cells mature, but the time of expression of CD11b is earlier than that of CD16. Accordingly, by using the anti-CD16 antibody and the anti-CD11b antibody as the second and third antibodies, respectively, and by obtaining the two-dimensional distribution map with the intensity of the fluorescence from the second and third fluorescence-labeled antibodies plotted along the two axes of the scattergram, immature granulocytes can be separated from mature neutrophils on the basis of difference in the intensity of the fluorescence for the second fluorescence-labeled antibody (see FIG. 4). Also the immature granulocytes can be classified into groups different in the degree of maturity on the basis of difference in the intensity of the fluorescence for the third fluorescence-labeled antibody (see FIG. 5).

Here, the classification of immature granulocytes into groups different in the degree of maturity means that promyelocytes, myelocytes, metamyelocytes and the like are classified into at least two groups of immature granulocytes and cells in each group can be enumerated.

The total immature granulocyte count and the immature granulocyte count in each of the groups different in the degree of maturity thus obtained are divided by the total leukocyte count obtained in step (3) to obtain the ratio or proportional count for each of the immature granulocyte counts to the total leukocyte count.

EXAMPLES

The method of classifying and counting immature granulocytes of the present invention is described in further detail by way of examples.

Example 1

Reagents having the following compositions were prepared:

① Fluorescence-labeled Antibodies
  (a) PerCP-labeled anti-CD45 antibody (produced by Becton Dickinson, Antil-Hle-1, the first antibody having red fluorescence)
  (b) FITC-fluorescence-labeled anti-CD16 antibody (produced by Becton Dickinson, Leu-11b, the second antibody having green fluorescence)
  (c) PE-labeled anti-CD11b antibody (produced by Becton Dickinson, Leu-15, the third antibody having orange fluorescece)

② Ammonium Chloride Base Hemolysing Agent
  (d) Ammonium chloride ($NH_4Cl$) 8.26 g/L
  (e) Potassium hydrogencarbonate ($KHCO_3$) 1.0 g/L
  (f) EDTA-4Na 0.037 g/L
  (g) Purified water Ten μL of the FITC-labeled anti-CD16 antibody, 10 μM L of the PE-labeled anti-CD11b antibody and 10 μL of the PerCP-labeled anti-CD45 antibody were added to 100 μL of peripheral blood anticoagulated with heparin. The resulting mixture was incubated for about 30 minutes at room temperature to fluorescence-stain leukocytes.

Then 2 mL of the ammonium chloride base hemolysing agent were added to the mixture, which was then incubated for five minutes at room temperature, thereby to hemolyse and remove erythrocytes which would disturb measurement of leukocytes.

Side scattered light and fluorescences having wavelengths of 530 nm (green), 585 nm (orange) and 650 nm (red) were measured with regard to the thus obtained hematological sample using a flow cytometer provided with an argon ion laser of 488 nm as a light source.

Figure 6:
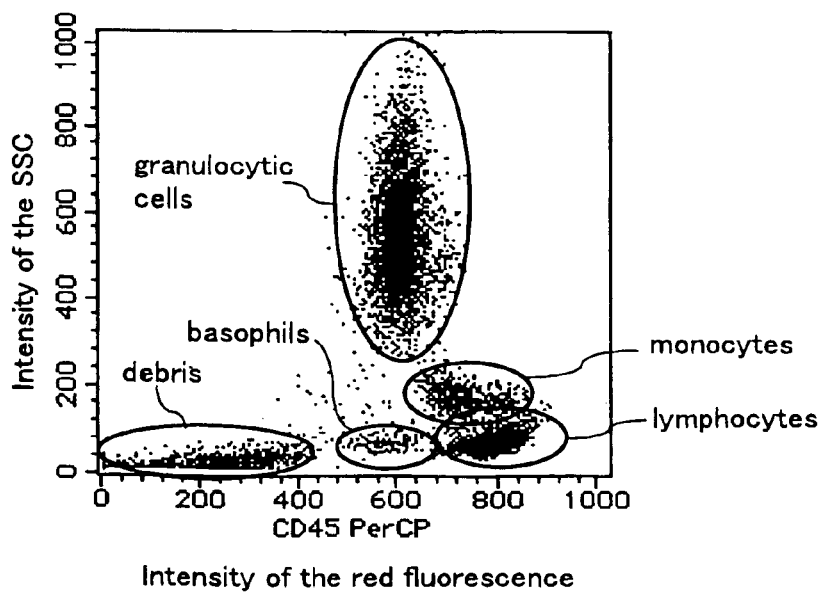
FIG. 6 is a scattergram showing distribution of individual cells with intensities of side scattered light and red fluorescence plotted in coordinate axes in accordance with Example 1.

FIG. 6 shows a scattergram with the intensity of the side scattered light and the intensity of the red fluorescence plotted in the coordinate axes, illustrating the distribution of cells in the sample. Five groups of granulocytes, monocytes, lymphocytes, basophils and debris were recognized as seen in FIG. 6. Analysis was made by enclosing all leukocytes with a window W1 and counting the total number of the enclosed leukocytes (see FIG. 7).

Figure 7:
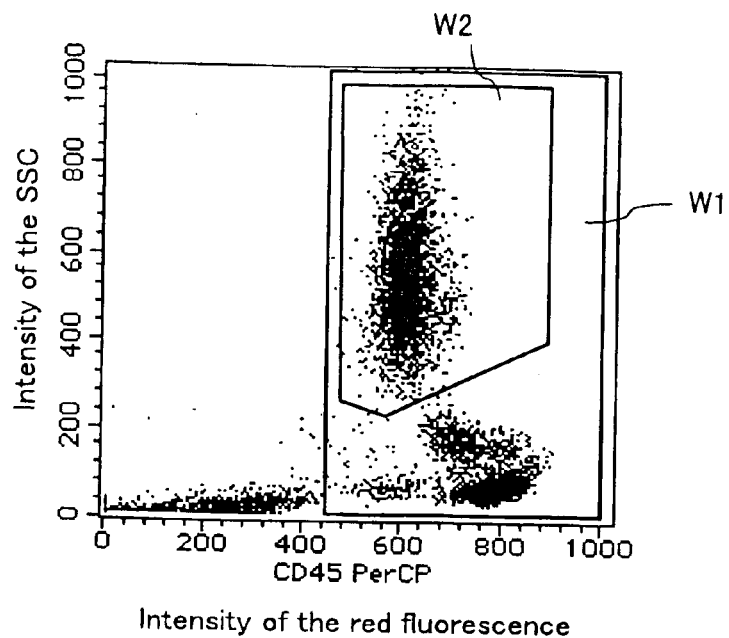
FIG. 7 is a scattergram showing distribution of all leukocytes and granulocytic cells (neutrophilic cells and eosinophils) in accordance with Example 1.

Also, granulocytes were enclosed within a window W2 in the same scattergram (see FIG. 7).

Figure 8:
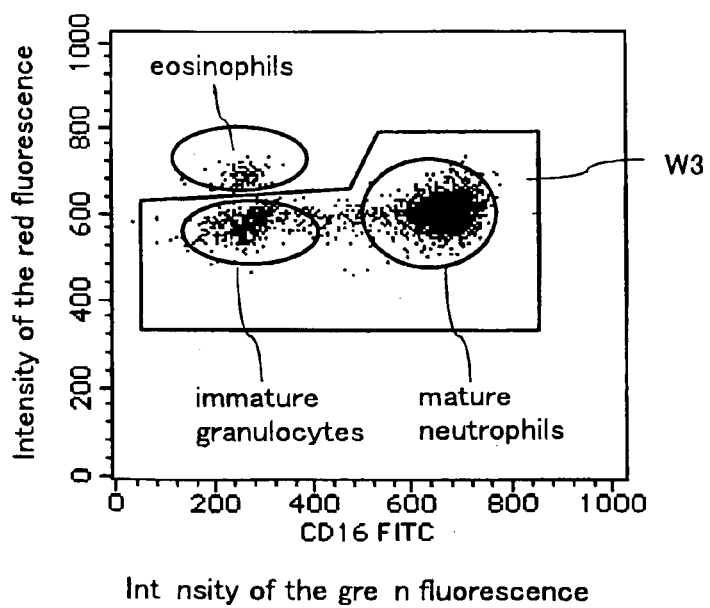
FIG. 8 is a scattergram showing distribution of eosinophils, immature granulocytes and mature neutrophils with intensities of red and green fluorescence plotted in the coordinate axes in accordance with Example 1.

FIG. 8 shows a scattergram with the intensity of the red fluorescence and that of the green fluorescence plotted in the coordinate axes, illustrating the distribution only of cells in window W2.

Three groups of eosinophils, immature granulocytes and mature neutrophils were recognized as seen in FIG. 8. Analysis was made by enclosing neutrophilic cells (immature granulocytes and mature neutrophils) within a window W3 as shown in FIG. 8.

Figure 9:
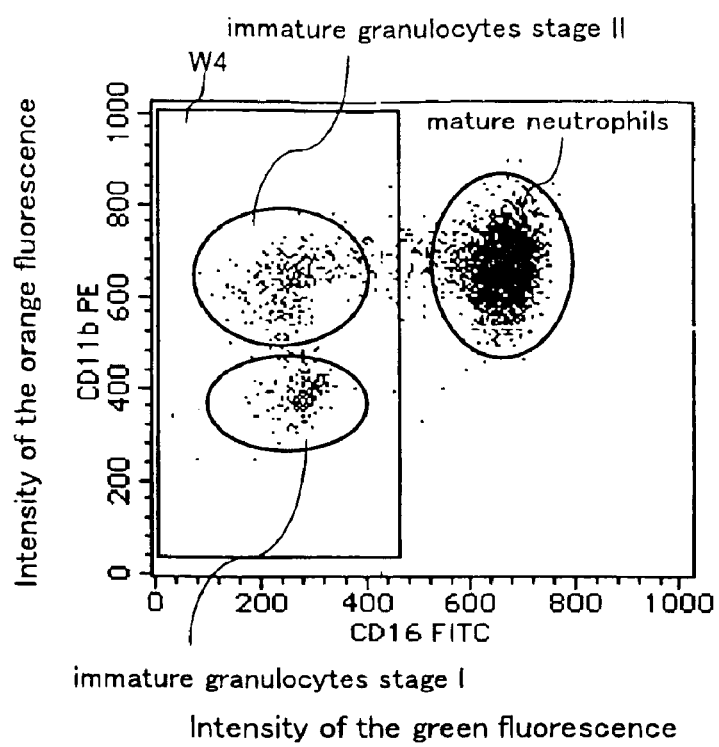
FIG. 9 is a scattergram showing distribution of stage-I immature granulocytes, stage-II immature granulocytes and mature neutrophils with orange and green fluorescence plotted in the coordinate axes in accordance with Example 1.

FIG. 9 shows a scattergram with the intensity of the orange fluorescent light and that of the green fluorescent light plotted in the coordinate axes, illustrating the distribution only of cells in window W3.

Three groups of immature granulocytes in a stage I, immature granulocytes in a stage II and mature neutrophils were recognized as seen in FIG. 9. Analysis was made by enclosing the two groups of immature granulocytes within a window W4 and counting the total number of the immature granulocytes.

Next, the total number of immature granulocytes was divided by the total number of the leukocytes counted above, thereby to obtain the ratio or proportional count of the immature granulocyte count to the total leukocyte count.

Separately from Example 1, immature granulocytes were analyzed by a manual microscopic method (May-Grünwald-Giemsa stain or other appropriate blood film stain, 800 WBC count) with use of a hematological sample which was substantially the same as used in Example 1.

Figure 10:
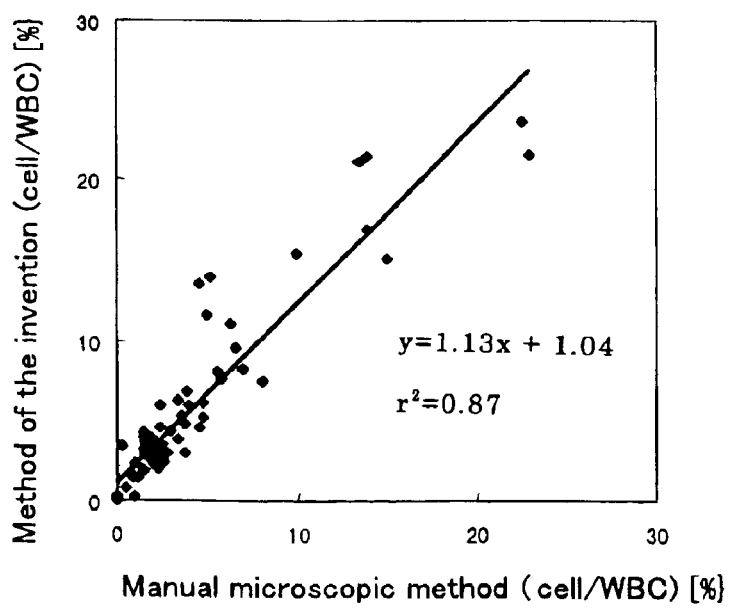
FIG. 10 is a graph showing correlation between an immature granulocyte count by the method of the present invention and that by a manual method.
Figure 11:
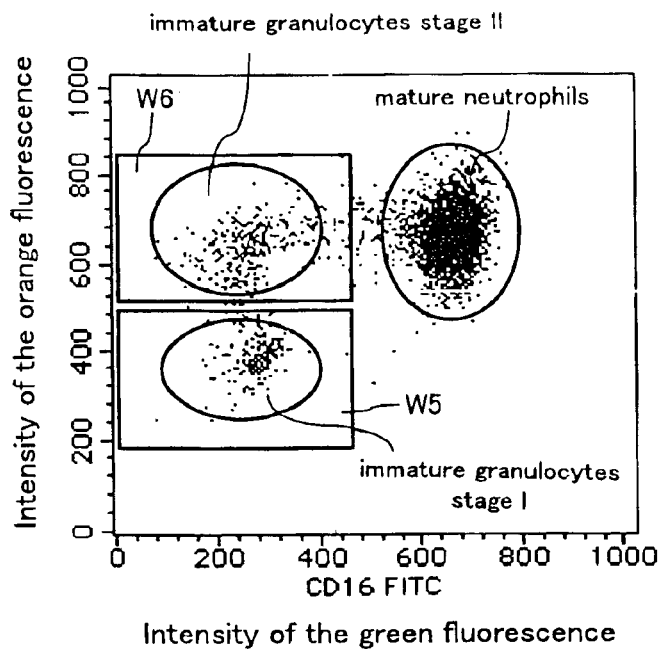
FIG. 11 is a scattergram showing distribution of stage-I immature granulocytes, stage-II immature granulocytes and mature neutrophils with orange and green fluorescence plotted in the coordinate axes in accordance with Example 2.

FIG. 10 is a graph showing correlation between the ratio or proportional count of the immature granulocytes count obtained with the flow cytometer in Example 1 and that obtained by the manual microscopic method.

As shown in FIG. 10, a correlation coefficient of $r^2=0.87$ and regression analysis of y=1.13x+1.04 was obtained, which showed that the method of Example 1 was remarkably accurate in classifying and counting immature granulocytes.

Example 2

Immature granulocytes in peripheral blood were measured by the same method as in Example 1. Analysis was made by enclosing the two groups of immature granulocytes with separate windows W5 and W6, counting the numbers of stage-I immature granulocytes in window W5 and stage-II immture granulocytes in window W6 and obtaining the ratios of the stage-I and stage-II immature granulocyte counts to the total leukocyte count.

Separately from Example 2, immature granulocytes of each type were analyzed by a manual microscopic method (May-Grünwald-Giemsa stain) with use of a hematological sample substantially the same as used in Example 2. Additionally, the stage-I immature granulocytes identified by the method of the invention correspond to promyelocytes and myelocytes identified by the manual microscopic method and the stage-II immature granulocytes identified by the method of the invention correspond to metamyelocytes identified by the manual microscopic method.

Figure 12:
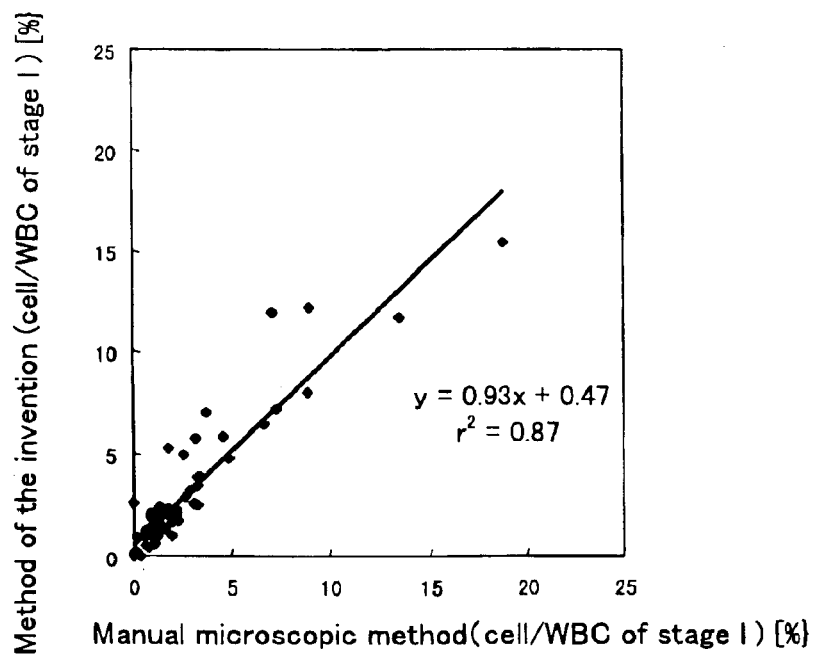
FIG. 12 is a graph showing correlation between the stage-I immature granulocyte count by the method of the present invention and that by the a manual method.
Figure 13:
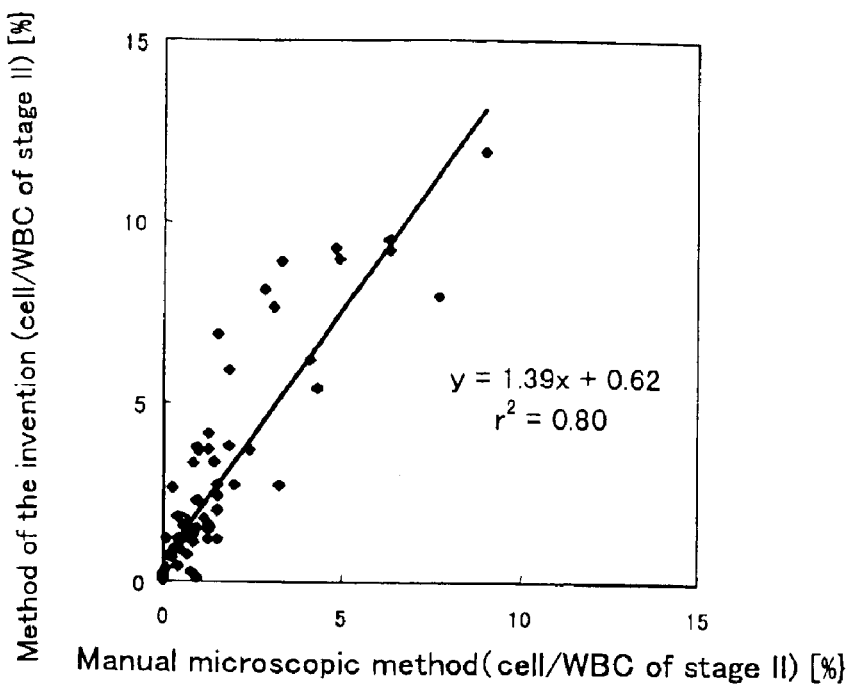
FIG. 13 is a graph showing correlation between the stage-II immature granulocyte count by the method of the present invention and that by the manual method.

FIG. 12 is a graph showing correlation between the ratio of the stage-I immature granulocyte count obtained with the flow cytometer in Example 2 and that obtained by the manual microscopic method. FIG. 13 is a graph showing correlation between the ratio of the stage-II immature granulocyte count obtained with the flow cytometer in Example 2 and that obtained by the manual microscopic method.

As regards the stage-I immature granulocytes, the correlation coefficient of $r^2=0.87$ and regression analysis of y=0.93x+0.47 was obtained as shown in FIG. 12, and as regards the stage-II immature granulocytes, the correlation coefficient of $r^2=0.80$ and regression analysis of y=1.39x+0.62 was obtained as shown in FIG. 13. These results showed that the method of Example 2 is remarkably accurate in classifying and counting immature granulocytes in each stage of maturity.

What is claimed is:
1. A method for classifying and counting leukocytes comprising the steps of:
  (1) adding to a hematological sample the following fluorescence-labeled antibodies labeled with fluorescent dyes which emit fluorescences distinguishable from each other:

(a) a first fluorescence-labeled antibody which binds specifically to leukocytes,
(b) a second fluorescence-labeled antibody which binds to at least one kind of neutrophilic cells, and
(c) a third fluorescence-labeled antibody which binds to at least one kind of immature granulocytic cells,
in order to stain the leucocytic cells in the hematological sample;

(2) removing erythrocytes from the hematological sample;
(3) analyzing the resulting hematological sample using a flow cytometer to measure at least one scattered light signal and three separate fluorescence signals;
(4) classifying granulocytic cells on the basis of intensity of the scattered light and intensity of fluorescence from the first fluorescence-labeled antibody;
(5) distinguishing eosinophils and neutrophilic cells in the granulocytic cells obtained in step (4) on the basis of the intensity of the fluorescence from the first fluorescence-labeled antibody and the intensity of the fluorescence from the second or third fluorescence-labeled antibody;
(6) classifying the neutrophilic cells obtained in step (5) into groups different in degree of maturity on the basis of the intensity of the fluorescence from the second fluorescence-labeled antibody and the intensity of the fluorescence from the third fluorescence-labeled antibody; and
(7) counting the number of cells in each of the groups.

2. A method according to claim 1, wherein in step (4), a group of all leukocytic cells is defined and counted on the basis of the intensity of the scattered light and the intensity of the fluorescence from the first fluorescence-labeled antibody in addition to the granulocytic cells obtained in step (4), and in step (6), the ratio of the number of the neutrophilic cells obtained in step (5) different in degree of maturity with respect to the number of all the leukocytic cells is calculated.

3. The method according to claim 1, wherein the first fluorescence-labeled antibody comprises an anti-CD45 antibody.

4. The method according to claim 1, wherein the second fluorescence-labeled antibody comprises an antibody selected from the group consisting of an anti-CD11b antibody, an anti-CD16 antibody, an anti-CD66b antibody and an anti-CD66c antibody, and the third fluorescence-labeled antibody comprises an antibody selected from the same group but different from the antibody of the second fluorescence-labeled antibody.

5. The method according to claim 1, wherein the scattered light measured is side scattered light.

6. The method according to claim 5, wherein the fluorescent dyes of the first, second and third fluorescence-labeled antibodies for emitting distinguishable fluorescences comprise a combination of FITC, PE and PE-CY5 or a combination of FITC, PE and PerCP.

7. The method according to claim 1, wherein the fluorescent dyes are selected from the group consisting of fluorescein isothiocyanate (FITC), phycoerythrin (PE), allophycocyanin (APC), Texas Red, PE-CY5 and peridinin chlorophyll protein (PerCP).

8. The method according to claim 1, wherein the hematological sample is a sample of peripheral blood, bone marrow fluid or urine of a mammal.

9. The method according to claim 1, wherein the leukocytic cells are fluorescence-stained after the erythrocytes are removed from the hematological sample.

10. The method according to claim 1 that in the step (5), a two-dimensional scattergram is produced from the intensity of the fluorescence from the first fluorescence-labeled antibody and the intensity of the fluorescence from the second or third fluorescence-labeled antibody, and the eosinophils and the group of neutrophilic cells in the granulocytic cells obtained in step (4) are distinguished on the two-dimensional scattergram.

11. The method according to claim 1 that in the step (4), a two-dimensional scattergram is produced from the intensity of the scattered light and the intensity of the fluorescence from the first fluorescence-labeled antibody, and the granulocytic cells obtained in step (4) are distinguished on the two-dimensional scattergram.

12. The method according to claim 1 that in the step (6), a two-dimensional scattergram is produced from the intensity of the fluorescence from the second fluorescence-labeled antibody and the intensity of the fluorescence from the third fluorescence-labeled antibody, and the neutrophilic cells are classified according to degrees of maturity on the two-dimensional scattergram.

13. A method for classifying and counting leukocytes comprising the steps of:
(1) adding to a hematological sample the following fluorescence-labeled antibodies labeled with fluorescent dyes which emit fluorescences distinguishable from each other:
(a) a first fluorescence-labeled antibody which binds specifically to leukocytes,
(b) a second fluorescence-labeled antibody which binds to at least one kind of neutrophilic cells, and
(c) a third fluorescence-labeled antibody which binds to at least one kind of immature granulocytic cells,
in order to stain the leucocytic cells in the hematological sample;
(2) removing erythrocytes from the hematological sample;
(3) analyzing the resulting hematological sample using a flow cytometer to measure at least one scattered light signal and three separate fluorescence signals;
(4) classifying granulocytic cells on the basis of intensity of the scattered light and intensity of fluorescence from the first fluorescence-labeled antibody;
(5) distinguishing eosinophils and neutrophilic cells in the granulocytic cells obtained in step (4) on the basis of the intensity of the fluorescence from the first fluorescence-labeled antibody and the intensity of the fluorescence from the second or third fluorescence-labeled antibody;
(6) classifying the neutrophilic cells obtained in step (5) into groups different in degree of maturity on the basis of the intensity of the fluorescence from the second fluorescence-labeled antibody and the intensity of the fluorescence from the third fluorescence-labeled antibody; and
(7) counting the number of cells in each of the groups;
wherein the second and third fluorescence-labeled antibodies comprise any combination of an anti-CD 16 antibody with an anti-CD11b antibody, an anti-CD 16 antibody with an anti-CD66b antibody, an anti-CD16 antibody with an anti-CD66c antibody, an anti-CD11b antibody with an anti-CD66b antibody, and an anti-CD11b antibody with an anti-CD66c antibody.

14. The method according to claim 13, wherein the second and third fluorescence-labeled antibodies comprise the anti-CD16 antibody and the anti-CD11b antibody.

15. A method for classifying and counting leukocytes comprising the steps of:
(1) adding to a hematological sample the following fluorescence-labeled antibodies labeled with fluorescent dyes which emit fluorescences distinguishable from each other:
   (a) a first fluorescence-labeled antibody which binds specifically to leukocytes,
   (b) a second fluorescence-labeled antibody which binds to at least one kind of neutrophilic cells, and
   (c) a third fluorescence-labeled antibody which binds to at least one kind of immature granulocytic cells,
   in order to stain the leucocytic cells in the hematological sample;
(2) after the adding step (1), removing erythrocytes from the hematological sample;
(3) analyzing the resulting hematological sample using a flow cytometer to measure at least one scattered light signal and three separate fluorescence signals;
(4) classifying granulocytic cells on the basis of intensity of the scattered light and intensity of fluorescence from the first fluorescence-labeled antibody;
(5) distinguishing eosinophils and neutrophilic cells in the granulocytic cells obtained in step (4) on the basis of the intensity of the fluorescence from the first fluorescence-labeled antibody and the intensity of the fluorescence from the second or third fluorescence-labeled antibody;
(6) classifying the neutrophilic cells obtained in step (5) into groups different in degree of maturity on the basis of the intensity of the fluorescence from the second fluorescence-labeled antibody and the intensity of the fluorescence from the third fluorescence-labeled antibody; and
(7) counting the number of cells in each of the groups.

* * * * *